United States Patent [19]

Lee et al.

[11] Patent Number: 4,898,920

[45] Date of Patent: Feb. 6, 1990

[54] ADHESIVE COMPOSITIONS, CONTROLLED RELEASE COMPOSITIONS AND TRANSDERMAL DELIVERY DEVICE

[75] Inventors: Chi-Long Lee, Midland; Katherine L. Ulman, Sanford, both of Mich.

[73] Assignee: Dow Corning Corporation, Midland, Mich.

[21] Appl. No.: 109,157

[22] Filed: Oct. 15, 1987

[51] Int. Cl.$^4$ ............................................. C08F 77/04
[52] U.S. Cl. ...................... 525/477; 525/479; 528/33; 524/268; 424/448; 424/449
[58] Field of Search ............... 525/477, 479; 528/33; 524/268; 424/448, 447, 449

[56] References Cited

U.S. PATENT DOCUMENTS

| | | | |
|---|---|---|---|
| Re. 25,727 | 2/1965 | Haluska et al. | 260/448.2 |
| 2,736,721 | 2/1956 | Dexter | 260/42 |
| 2,814,601 | 11/1957 | Currie et al. | 525/478 |
| 2,868,824 | 1/1959 | Haluska et al. | 260/448.2 |
| 3,057,469 | 10/1962 | Bond | 525/477 |
| 3,387,061 | 6/1968 | Smith et al. | 260/874 |
| 3,483,240 | 12/1969 | Boudreau | 260/448.2 |
| 3,527,842 | 9/1970 | Clark | 260/825 |
| 3,528,940 | 9/1970 | Modic | 525/477 |
| 3,541,127 | 11/1970 | Beattie et al. | 260/448.8 |
| 3,699,963 | 10/1972 | Zaffaroni | 128/268 |
| 3,731,683 | 5/1973 | Zaffaroni | 128/268 |
| 3,734,097 | 5/1973 | Zaffaroni | 128/268 |
| 3,742,951 | 7/1973 | Zaffaroni | 128/268 |
| 3,797,494 | 3/1974 | Zaffaroni | 128/268 |
| 3,819,745 | 6/1974 | Plante | 528/33 |
| 3,957,843 | 5/1976 | Bennett | 260/448.2 B |
| 3,965,150 | 6/1976 | Moeller | 260/486 R |
| 3,983,298 | 9/1976 | Hahn et al. | 525/477 |
| 3,996,934 | 12/1976 | Zaffaroni | 128/268 |
| 4,151,319 | 4/1979 | Sackoff et al. | 428/40 |
| 4,235,988 | 11/1980 | Fildes et al. | 528/79 |
| 4,286,592 | 9/1981 | Chandrasekaran | 128/260 |
| 4,463,115 | 7/1984 | Hirose et al. | 524/188 |
| 4,584,337 | 4/1986 | Lee et al. | 524/500 |
| 4,591,622 | 5/1986 | Blizzard et al. | 525/477 |
| 4,600,751 | 7/1986 | Lee et al. | 525/404 |

FOREIGN PATENT DOCUMENTS

| | | |
|---|---|---|
| 1106993 | 8/1981 | Canada . |
| 0188895 | 7/1986 | European Pat. Off. ............... 283/12 |
| 3502928 | 1/1985 | Fed. Rep. of Germany . |
| 1361668 | 4/1964 | France . |
| 59-36608 | 2/1984 | Japan . |
| 59-36609 | 2/1984 | Japan . |
| 1201778 | 8/1970 | United Kingdom . |
| 2115431 | 9/1983 | United Kingdom . |

OTHER PUBLICATIONS

Langer, Chem. Eng. Commun., vol. 6, pp. 1–48 (1980).
Tojo, et al., J. of Cont. Rel., vol. 1, pp. 197–203 (1985).
Tojo, et al., AIChE J., vol. 31, No. 5, pp. 741–746 (1985).
Sun, et al., Drug. Dev. & Ind. Pharmacy, vol. 12, No. 3, pp. 327–348 (1986).
Lee, et al., Drug Dev. & Ind. Pharmacy, vol. 12, pp. 349–368 (1986).
Lee, et al., Drug Dev. & Ind. Pharmacy, vol. 12, No. 3, pp. 369–383 (1986).
Mariann, et al., Proced. Intern. Symp. Control. Rel. Bioact. Mater., vol. 14, (1987).
Pfister, et al., Proceed. Intern. Symp. Control. Rel. Bioact. Mater., vo. 13, pp. 220–221 (1986).

*Primary Examiner*—John C. Bleutge
*Assistant Examiner*—R. Dean, Jr.
*Attorney, Agent, or Firm*—Marshall, O'Toole, Gerstein, Murray & Bicknell

[57] ABSTRACT

Adhesive compositions comprising blends of polyethylene oxide-grafted silicone polymers with resinous copolymers are disclosed. The adhesive compositions enhance release, in a controlled fashion, of bioactive or chemical agents blended or otherwise dispersed through the compositions. Transdermal drug delivery devices incorporating the adhesive compositions are also disclosed.

24 Claims, No Drawings

ADHESIVE COMPOSITIONS, CONTROLLED RELEASE COMPOSITIONS AND TRANSDERMAL DELIVERY DEVICE

BACKGROUND OF THE INVENTION

1. Field of the Invention

This invention relates generally to silicone based adhesive compositions and, more particularly, this invention relates to silicone/organic adhesive copolymers and compositions, and devices made therefrom for controlled release of bioactive or chemical agents.

2. Description of Related Art

Pressure sensitive adhesives and other adhesives containing silicone or organic polymers, including graft copolymers, are well known. However, prior art adhesives tend to be either hydrophobic or hydrophilic in nature, rendering them unsuitable for applications wherein conditions incompatible with the adhesive's hydrophobic or hydrophilic nature are encountered.

Also, many prior art adhesives based on silicone or organic graft copolymers are of types which are incapable of being formulated to satisfy particular requirements with respect to adhesion to specific substrates, liquid and/or gas permeability or impermeability, and release of active agents to the substrate at a controlled rate, or removal of undesirable agents from the substrate.

There has long been a need for adhesives which are capable of adhesion to a wide variety of substrates and which are adaptable to various environments and conditions. Of special interest are pressure sensitive adhesives which offer numerous advantages in industrial as well as health-related applications.

Adhesives are widely used in agricultural, industrial or health-related applications wherein it is desired to release an active agent such as a herbicide, insecticide, drugs or other bioactive agents at a controlled rate for sustained time periods. Such adhesives ideally should be capable of being loaded with sufficiently high concentrations of the agent to be released for the desired application, should release the agent into the surrounding atmosphere or underlying substrate in a controlled fashion, preferably at a uniform rate, over the desired period of use and, especially in agricultural or health-related fields, not directly harm or contribute to harm of the underlying substrate. The adhesion of such materials should be sufficiently great that the adhesive remains adhered to the substrate, yet not be so great as to cause trauma to the substrate upon removal of the adhesive.

In industrial applications, pressure sensitive adhesives are widely used in composite structures and other applications to bond two or more layers or surfaces of similar or dissimilar materials to each other. Such adhesives should provide as high adhesion to each substrate as possible in order to ensure the integrity of the structure over the desired time period of use and under the temperature and moisture conditions encountered in use.

The use of pressure sensitive adhesives in transdermal drug delivery devices is well known. Generally, in such devices a layer of a pressure sensitive adhesive loaded with a drug or other bioactive agent is adhered to a backing layer, e.g. a bandage, which is applied to a user with the pressure sensitive adhesive directly in contact with the user's skin.

Such devices are generally packaged with a release liner disposed over the surface of the pressure sensitive adhesive layer.

Ideally, the drug or other agent loaded into the pressure sensitive adhesive layer will be released therefrom and migrate through the user's skin at a desired rate in order to provide a uniform rate of drug delivery to the user. A uniform rate of drug delivery is desirable in that, ideally, the concentration of a drug in a user's bloodstream should be maintained above the minimum therapeutic level and below the level at which undesirable side effects occur.

Other desirable characteristics of pressure sensitive adhesives useful in transdermal drug delivery devices are sufficiently high adhesiveness to skin, to the backing layer and to the release liner to ensure the integrity of the drug delivery device. However, the adhesion between the adhesive layer and the release liner must not be so high as to hinder removal of the release liner, and the adhesion to skin must not be so high as to cause trauma during removal of the device.

Also, the device as a whole including the backing layer and adhesive layer should be sufficiently permeable to the passage of oxygen and water vapor to avoid damage to the underlying skin. The adhesive should not lose its adhesive properties on contact with water, nor should the adhesive lose its adhesive properties upon aging.

The rate of release of a bioactive agent should be uniform with respect to time. The permeability coefficient of the bioactive agent through the skin varies with the individual user depending on race, the position on the body, and other factors known in the art. The permeability coefficient is the product of the diffusion coefficient and the solubility coefficient associated with the materials of construction.

Another advantageous property of an adhesive useful in a transdermal drug delivery device is a sufficiently high tack, which is a measure of how quickly adhesion between the adhesive layer and substrate occurs.

Ideally, the pressure sensitive adhesive should not only act merely as a carrier for the bioactive agent but should also enhance the rate of release of the agent.

Some prior art transdermal drug delivery devices utilize adhesives which exhibit excessively high or poorly controlled adhesion to the skin, so as to cause trauma such as skin tearing, removal of epidermis, pulled hair, or bruises upon removal.

A major problem with prior transdermal drug delivery devices is their inability to provide either highly uniform release rates as the concentration of the drug or other bioactive agent in the device decreases, or a release rate which is sufficiently high to provide a therapeutic concentration of drug or other bioactive agent in the user's blood without attaining a concentration which is so high as to cause undesirable side effects.

Others have insufficient permeability to oxygen and water vapor such that edema, blistering, or wrinkling or discoloration of skin occurs.

Further, another major problem with currently available medical grade pressure sensitive adhesives is their tendency to dry out and lose all or most of their tack upon aging. This is especially evident in pressure sensitive adhesives loaded with drugs containing amine functionality.

SUMMARY OF THE INVENTION

It is an object of the invention to overcome one or more of the problems described above.

According to the present invention, an adhesive composition comprises a silicone/organic random graft copolymer, optionally blended with a resinous random silicone copolymer The graft copolymer includes polyethylene oxide side chains which impart increased solubility of hydrophilic bioactive agents in the polymer matrix thus enhances the rate of release of bioactive agents. The siloxane backbone of the graft copolymer enhances the gas permeability of the system.

The inventive adhesive may be used in a wide variety of industrial, agricultural, and health-related applications.

The invention also comprehends a controlled release composition wherein an active agent, such as a drug or other bioactive agent, for example, is blended with or otherwise dispersed throughout the adhesive composition of the invention. The adhesive may be in either a cured or an uncured state. The invention further comprehends a transdermal drug delivery device wherein the drug release composition is disposed on a backing layer such as a bandage with a release liner disposed over the adhesive layer.

Other objects and advantages of the invention will be apparent to those skilled in the art from the following detailed description, taken in conjunction with the appended claims.

DETAILED DESCRIPTION OF THE INVENTION

General

According to the invention, an adhesive composition is provided which consists essentially of a random graft copolymer optionally blended with a resinous random copolymer.

The random graft copolymer has the average formula

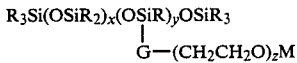

wherein
x/y is in the range of 0.01 to 100, inclusive;
x+y is in the range of 10 to 1000, inclusive;
z is a number less than or equal to 15;
R is a monovalent hydrocarbon radical selected from alkyl groups having 1 to 8 carbon atoms, aryl groups, and haloalkyl groups;
all R groups can be the same or different;
M is H, —COCH=CH$_2$ or C(O)NH(CH$_2$)$_2$O(O)C-Ne=CH$_2$; and,
G is a divalent radical selected from —CH$_2$CH$_2$O—, —CH$_2$CH$_2$CH$_2$O—, and urethane groups such as —R$^1$NR$^4$C(O)NHR$^2$NHC(O)O— wherein R$^1$ is a divalent alkylene group, R$^2$ is an alkylene or an arylene group, and R$^4$ is H or CH$_3$.

The random graft copolymer is preferably blended with a resinous random copolymer consisting essentially of structural units having the formulae R$_3$$^3$SiO$_{0.5}$ and SiO$_2$ wherein R$^3$ is a monovalent hydrocarbon radical, the resinous random copolymer having an SiOH functionality of at least about 0.5 wt. %.

The graft copolymer is present in the adhesive composition at a level of about 10 to 100 wt. %. The resinous copolymer thus constitutes 0 to 90% wt. of the composition. The foregoing percentages are based on the total weight of the graft and resinous copolymers.

Preferably, the resinous copolymer is present at a level of at least about 1 wt. %, highly preferably at a level of at least about 5 wt. %, and most highly preferably at about 30 to 70 wt. % (based on the total weight of the graft and resinous copolymers).

The adhesive composition can be uncured if desired, although uncured materials tend to lack cohesive strength. (The need for cohesive strength varies with the application.) If curing is desired, it may be carried out by any of a number of conventional methods.

The adhesive composition of the invention may be used as a pressure sensitive adhesive if desired, and is also useful in agricultural and other applications wherein pressure need not be applied to effect adhesion. The tack of the adhesive composition can be controlled as described below.

To form a controlled release composition, a drug or other chemical or bioactive agent is blended with or otherwise dispersed throughout the adhesive composition, in either a cured or uncured state. The composition is especially useful in drug release compositions containing hydrophilic drugs such as certain steroids. The adhesive composition preferably but not necessarily contains resinous copolymer.

The drug release composition of the invention may be incorporated into a transdermal drug delivery device wherein the adhesive drug release composition is disposed over a backing layer such as a bandage, preferably with a release liner disposed over the opposite surface of the adhesive layer.

According to the invention, by varying the composition of the graft copolymer, the composition of the resinous copolymer, and the loading level of the resinous copolymer in the composition, an adhesive composition having a desirable predetermined level of adhesion to various substrates and a desired range of release rates may be obtained, thus providing a controlled release composition wherein controlled release of drugs, other bioactive agents or chemicals is attained.

Having described the invention in general terms, the constituents and characteristics of the invention will now be described in greater detail.

The Graft Copolymer

The graft copolymer of the invention, generally speaking, has a siloxane backbone grafted randomly with polyethylene oxide units.

The generalized formula for the graft copolymer is given as follows:

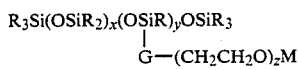

wherein
x/y is in the range of 0.01 to 100, inclusive;
x+y is in the range of 10 to 1000, inclusive;
z is a number less than or equal to 15;
R is a monovalent hydrocarbon radical selected from alkyl groups having 1 to 8 carbon atoms, aryl groups, and haloalkyl groups;
all R groups can be the same or different;
M is H, —COCH=CH$_2$ or C(O)NH(CH$_2$)$_2$O(O)C-Me=CH$_2$; and, G is a divalent radical selected from —CH$_2$CH$_2$O—, —CH$_2$CH$_2$CH$_2$O—, and urethane groups such as —R$^1$NR$^4$C(O)NHR$^2$NHC(O)O— wherein R$^1$ is a divalent alkylene group, R$^2$ is an alkylene or an arylene group, and R$^4$ is H or CH$_3$.

Hydrophilicity of the graft copolymer is imparted by the polyethylene oxide units. The hydrophilicity of the molecule can be controlled by variation of the size of the polyethylene oxide units, i.e. control of the number z, as well as by variation of the proportion of the number of side chains y per molecule to the number of total siloxane units (x+y), i.e. by control of the proportion of y/(x+y).

The hydrocarbon group R is preferably alkyl and highly preferably methyl. Although the R groups can be the same or different, it is highly preferred that substantially all R groups be methyl groups.

When used in a controlled release composition, release rates of drugs or other agents generally decrease as alkyl groups higher than methyl are used in the siloxane backbone.

Methyl groups are preferred as they provide the highest drug release rate, and reagents providing these groups are generally commercially available and are relatively inexpensive.

Aryl groups may be unsubstituted, or substituted with alkyl groups.

Haloalkyl groups such as, for example, trifluoropropyl groups or other halogen substituted alkyl groups known in the siloxane art, may also be utilized.

Although the molar ratio x/y is generally within the range of 0.01 to 100, it is preferred that the ratio of y/(x+y) be in the range of about 0.1 to 0.5, inclusive. If the grafted siloxane units represented by y comprise less than about 10 mole % of the total of siloxane units (x+y), adhesion is satisfactory but drug release rates of hydrophilic drugs are not significantly enhanced since insufficient hydrophilicity is imparted to the composition. If the grafted units (y) comprise more than about 50 molar % of the backbone, the graft copolymer may be incompatible with the resinous copolymer.

It is highly preferred that the weight ratio of total siloxane groups to pendant ethylene oxide units be about 1.5:1.

The degree of polymerization (DP) is defined as the total (x+y) and is a measure of the size of the graft copolymer molecule. Expressed differently, the degree of polymerization is the total number of siloxane units in the molecule. The bigger the molecule is, the higher is its viscosity. It is desirable that the viscosity of the material be such that the material is in a fluid state at ambient conditions as this facilitates compounding.

Changes in the degree of polymerization principally affect adhesion but do not have an appreciable effect on the release rate of the composition.

Generally speaking, the degree of polymerization (x+y) can range from about 10 to 1000 with a range of 100 to 500 generally preferred. If the degree of polymerization is greater than 1000, it is difficult to prepare the copolymer as gelation occurs rather readily.

As molecular weight (i.e. degree of polymerization) increases, the cohesive strength of the graft copolymer increases. At a DP of less than 100, the graft copolymer may lack sufficient cohesive strength for practical purposes.

z may be any number less than or equal to about 15 with materials imparting a z value of about 1 to 12.5 being conveniently commercially available.

It should be understood that the z value in the structural formula of the graft copolymer is an average value.

If z is greater than 15, the graft copolymer is rendered so hydrophilic that membranes made therefrom disintegrate in contact with water.

Hydrophilicity is determined in part by the z value, while adhesion is determined at least in part by the hydroxyl functionality of the molecule. As z increases, the weight percent of hydroxyl functionality in the molecule decreases, and adhesion drops.

The linking group G is selected from ethylene oxide, propylene oxide, and urethane groups. Each of these has been found to be especially convenient in the preparation of the graft copolymer.

The graft copolymer can readily be prepared as demonstrated by the following reaction scheme wherein the use of methyl groups (Me) is exemplified:

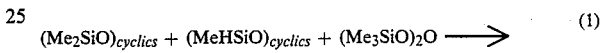

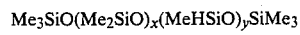

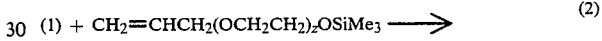

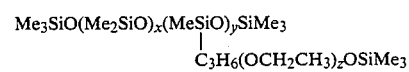

In practice, reaction (2) is monitored by infrared spectroscopy for a reduction in the SiH peak at 2140 cm$^{-1}$.

Following reaction (2), the trimethylsilyl group is hydrolyzed, as follows:

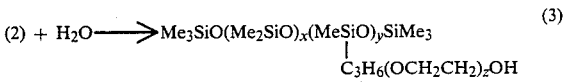

Endcapping with acrylate functionality is accomplished as follows:

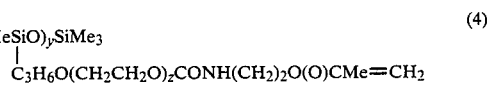

Reaction (1) is carried out at 100° C. using either CF$_3$SO$_3$H or Amberlyst 15 ion exchange resin as a catalyst. The product is filtered over CaCO3 before proceeding with reaction (2).

Reaction (2) is preferably carried out with reflux using 30 wt. % toluene or THF as a solvent and H$_2$PtCl$_6$·6H$_2$O as a catalyst.

In the foregoing reaction scheme, the values of x and y as well as the ratio x/y are controlled by variation of the respective cyclosiloxanes. All reagents are commercially available.

The graft copolymer may be prepared neat, in waterborne form, or in an organic solvent.

Further details of the graft copolymer preparation scheme are presented in Lee, et al. U.S. Pat. Nos.

4,584,337 (April 22, 1986) and 4,600,751 (July 15, 1986), the respective disclosures of which are hereby incorporated herein by reference.

The Resinous Copolymer

The resinous random copolymer used in the invention consists essentially of structural units having the formulae $R_3^3SiO_{0.5}$ and $SiO_2$ wherein $R^3$ is a monovalent hydrocarbon, and preferably alkyl groups having 1 to 8 carbon atoms. $R^3$ is preferably methyl. The copolymer has an SiOH functionality of at least about 0.5 wt. %.

The resinous copolymer comprises between 0 and 90 wt. % of the adhesive composition, and highly preferably comprises at least about 50 wt. % of the composition, with a concentration in the range of about 30 to 70 wt. % being preferred. A concentration of at least 1 wt. %, and generally 5 wt., is typically desirable. The resinous copolymer preferably has a number average molecular weight (Mn) in the range of about 2000 to 9000, with an upper limit of about 6000 being preferred.

The molecular weight of the resinous copolymer is closely related to the molar ratio of the $R_3^3SiO_{0.5}$ units to $SiO_2$ units in the copolymer chain. As the proportion of $R_3^3SiO_{0.5}$ units increases, the molecular weight decreases endcapping. Thus, a copolymer having a $R_3^3SiO_{0.5}/SiO_2$ molar ratio of 2:1 may have a molecular w of about 2000, while a copolymer having a molar ratio of 0.7:1 may have a molecular weight of about 8400. A 1:1 molar ratio typically results in a copolymer having a molecular weight of about 5900.

At molecular weights lower than about 2000, the resinous copolymer provides insufficient adhesion for most purposes. At molecular weights greater than 6000, the adhesive tack of the resinous copolymer is insufficient for most purposes.

The SiOH functionality of the resinous copolymer can be varied so as to provide "body" to the composition without curing. It is extremely difficult to prepare a copolymer having more than 5–6 wt. % hydroxyl functionality, and a range of 0.5–5 wt. % is most commonly encountered. Hydroxyl functionality in the range of 1–3 wt. % is preferred.

Adhesion drops off dramatically at hydroxyl functionalities less than about 0.5 wt. %.

If desired, the resinous copolymer may be encapped, preferably in the form of hydroxyl, vinyl, acrylate, or mercapto functional groups.

The loading level of the resinous copolymer in the adhesive composition depends on a number of factors including the molecular weight of the graft copolymer, the molecular weight of the resinous copolymer, the type of functionality (if any) of the graft copolymer and the amount of functionality on the graft copolymer. For a given molecular weight of resinous copolymer, an increase in the loading level of resinous copolymer increases adhesion of the composition up to a maximum point; loading above this point results in a dramatic drop-off of adhesion due to drying.

By varying the loading level of the resinous copolymer in the composition, the release rate of a given drug from the adhesive composition may be controlled. Generally, the release rate is at a maximum in the adhesive composition when no resinous copolymer is present. The release rate decreases as a direct function of the loading level of resinous copolymer. For example, with certain drugs with no resinous copolymer present, a release rate (dQ/dt) value of $33 \times 10^{-5}$ mcg/cm-sec. will be obtained. With a 50% resinous copolymer loading level, the release rate value will drop to $5.0 \times 10^{-5}$ mcg/cm-sec.

A method for the preparation of resinous copolymers of this type is described in detail in Dexter U.S. Pat. No. 2,736,721 (Feb. 28, 1956), the disclosure of which is hereby incorporated herein by reference.

Curing

If desired, the adhesive composition of the invention may be cured by any of a wide variety of means including free radical polymerization, typically using well known peroxide cure catalysts, or by other means known in the art, such as crosslinking through acrylate functional groups via radiation (including ultraviolet, electronic beam, infrared, microwave, X-ray and $\gamma$-radiation), free radical, redox and platinum catalyzed techniques.

The resinous copolymer provides reinforcement as well as adhesion, and the composition can be provided with more or less "body" by control of the hydroxyl functionality of the resinous copolymer. ("Body" increases with an increase in SiOH functionality.)

In one preferred form, an adhesive composition including a resinous copolymer as described herein is cross-linked to form a membrane which can be loaded with a drug or other bioactive agent.

The adhesive compositions comprising a blend of the graft copolymer and the resinous copolymer (or the graft copolymer alone) need not be cured; any solvent or water present may be removed and the resulting composition used "as is" or further compounded before ultimate use.

Controlled Release Adhesive Compositions

According to the invention, any of a wide variety of agents, such as hydrophobic or hydrophilic drugs or other bioactive agents, herbicides, insecticides, and industrial or other chemicals, can be blended or otherwise dispersed through the adhesive composition of the invention in order to provide a controlled release adhesive composition. The adhesive matrix can be in cured or uncured form.

Typical drugs can include steroids such as, for example, progesterone, testosterone, hydrocortisone, and $\beta$-estradiol. Antihistamines such as chlorophinaramine, antihypertensives such as clonidine, antismoking drugs such as nicotine, antianginal drugs such as nitroglycerine, and antiinflammatory drugs such as indomethacine are also suitable candidates for drug delivery using the controlled release adhesive composition of the invention.

By loading such drugs into the adhesive composition of the invention, a controlled uniform rate of release can be obtained. While prior drug release adhesive compositions are capable of loading only up to about 2 wt. %, it has been found that the adhesive composition of the invention can readily accommodate up to at least about 10 wt. % loading.

Transdermal Drug Delivery Device

The controlled release adhesive composition of the invention is well suited for incorporation into a transdermal drug delivery device wherein the adhesive controlled release composition is disposed as a layer on a backing layer such as a bandage with a release liner adhered to the adhesive composition surface opposite the backing layer.

The backing layer is preferably gas permeable which, in combination with the highly permeable adhesive layer provides a number of advantages over the prior art in addition to the attainment of controllable uniform drug release rates. For example, given the high permeability imparted to the adhesive composition by the siloxane component of the graft copolymer, rapid water evaporation through the delivery devices protects skin from damage. Also, since the adhesive strength of the composition can be controlled within desired limits, the adhesion can be predetermined so as to avoid trauma to the skin upon removal of the transdermal drug delivery device.

Suitable release liners include the commercially available products of Dow Corning Corporation (Midland, Mich. USA) designated Bio-Release ® liner and Syl-Off ® 7610 liner. Each of these liners has been tested with hydrophilic pressure sensitive adhesives of the invention and found to provide satisfactory release adhesions of less than 5 g/in.

The transdermal drug delivery device can include, if desired, a primer between the substrate (e.g. bandage) and the adhesive layer.

Other Applications

The adhesive composition of the invention is well suited for industrial use as a pressure sensitive adhesive, both for use in composite structures and in the adhesion of objects to underlying substrates such as metal (e.g. stainless steel), plastics, other polymers, wood, and the like. In such applications the adhesive composition will generally not contain a chemical or bioactive agent.

The adhesive composition of the invention can be used to deliver any of a wide variety of chemical agents, by controlled release, in industrial or agricultural applications. For example, a herbicide or insecticide can be blended with or otherwise dispersed throughout the adhesive composition, which can then be sprayed, preferably in emulsion form, on fields of growing crops. The herbicide or insecticide-bearing composition will adhere to the crops and release the herbicide or insecticide directly to the growing plant or to the atmosphere.

Tests have demonstrated that pressure sensitive adhesives of the invention can be loaded with Dursban ® chlorpyrifos insecticide ( a product of Dow Chemical Company) (e.g. for termites) or atrazine herbicide and provide controlled release.

Each of Dursban ® chlorpyrifos insecticide and atrazine herbicide were tested for capsule type release from an inventive adhesive composition consisting of 50 wt. % of a resinous copolymer (Mn =about 2900, 2-6 wt. % SiOH, $R_3{}^3SiO_{0.5}/SiO_2$ molar ratio of 1:1) and 50 wt. % of a 10% $Z_8$ copolymer. Each agent was released in a controlled, uniform manner. The release rate (dQ/dt×1) for Dursban ® insecticide was $1.01 \times 10^{-5}$ mcg/cm-sec. The release rate for atrazine was $2.95 \times 10^{-4}$ mcg/cm-sec.

It is possible to incorporate pheromones in the adhesive composition of the invention for application to trees or other surfaces in an area populated by insects to disrupt insect reproduction. The pheromones are preferably provided in the chemical delivery device in a very high concentration so as to saturate the surrounding area with pheromone released from the device. The dispersed pheromone attracts male insects, thus diverting them from the female, resulting in greatly reduced reproduction rates. Thus, the invention may have great utility in insect population control.

Experimental results have demonstrated controlled release of trimedlure pheromone from adhesives of the invention.

Trimedlure pheromone was tested for capsule type release from a 10% $Z_8$ graft copolymer/50 wt. % resinous copolymer adhesive composition, and controlled release at a rate of $1.53 \times 10^{-5}$ mcg/cm-sec. was observed.

EXAMPLES

The following specific examples are given in order to illustrate the practice of the invention, but are not to be considered limiting in nature.

Throughout the examples, graft random copolymers using polydimethylsiloxane (PDMS) units were prepared as generally described above. In most cases, such graft copolymers are identified by a designation generally of the form "$A\%Z_B$" wherein A is defined as $[y/(x+y)] \times 100$ (i.e. the average molar percentage of siloxane groups which contain grafted polyethylene oxide side chains). B is defined as the average z value of the graft copolymer i.e. the number of ethylene oxide units per pendant polyethylene oxide side chain.

Thus, a graft copolymer designated "10% $Z_4$" is one in which, on average, 10 mole % of the siloxane units are grafted with a polyethylene oxide side chain having an average of 4 ethylene oxide units.

Unless stated otherwise, the resinous random copolymer used in the composition was a trimethylsiloxane/silicate resin having a number average molecular weight (Mn) of about 5900, with about 2.6 wt. % hydroxyl functionality, and a $R_3{}^3/SiO_2$ molar ratio of about 1:1.

Example I

Preparation of Graft Copolymers $Z_4$ copolymer was prepared according to the following reaction scheme:

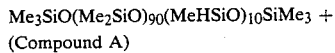
(Compound A)

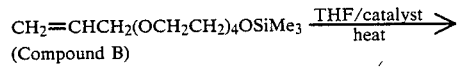
(Compound B)

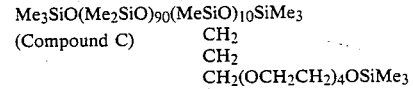
(Compound C)

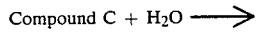

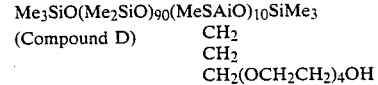
(Compound D)

Me₂SiO/MeHSiO Copolymer

The Me₃SiO(Me₂SiO)₉₀(MeHSiO)₁₀SiMe₃ copolymer (Compound A) was prepared by equilibrating 296 g (4.0 moles) of (Me₂SiO) (cyclic) with 27 g (0.44 mole) of (MeHSiO) (cyclic) and 7.2 g (0.0444 moles) of (Me₃Si)₂ O endblocking agent overnight, at 100° C. (in the presence of 1.5 g of Amberlyst ® 15 sulfonic acid ion exchange resin) in a 500 ml round bottom flask fitted with a thermometer, water cooled condenser, air driven stirrer, and heating mantle. Once the equilibration was complete, the catalyst was removed by pressure filtration, then the copolymer was used as is.

$CH_2=CHCH_2(OCH_2CH_2)_4OSiMe_3$ Polymer

An OH functional allyl glycol with an average of 4 ethylene oxide units per molecule, i.e. $CH_2=CHCH_2(OCH_2CH_2)_4OH$, (750 g, ~3.4 moles) and hexamethyldisilazane (700 g, 4.0 moles) were loaded into a 2 liter reaction vessel, warmed to ~120° C., and purged with dry nitrogen while maintaining the temperature at 20° C. overnight (with stirring). The following day an IR spectrum showed only trace amounts of OH between 3600-3200cm$^{-1}$. Unreacted hexamethyldisilazane was distilled through a J-head condenser and the pot residue was analyzed for pH. Since the pH was ~10, it was adjusted (by adding phosphoric acid) to a pH of ~7.4. The mixture was then stripped on a rotary stripper at 85° C. for two hours and used as is.

Hydrophilic Copolymers

About 109 g (0.15 moles of SiH) of $Me_3SiO(Me_2SiO)_{90}(MeHSiO)_{10}SiMe_3$, 46 g (0.15 moles $CH_2=CH_2—$) of $CH_2=CHCH_2(OCH_2CH_2)_4OSiMe_3$, and 100 ml of tetrahydrofuran were charged into a reaction vessel, warmed to reflux (~76° C.) and catalyzed with 0.1 ml of 0.04M $H_2PtCl_6.6H_2O$. The temperature was maintained at ~76° C. for 26 hours during which time an additional 0.3 ml of catalyst was added. An IR spectrum at this point showed all of the SiH (2140 cm$^{-1}$ was consumed. The polymer was washed with 200 ml of boiling water (to remove the trimethylsilyl group), separated, and stripped of volatiles at 85° C. under ~1 mm of Hg for about 2 hours. This polymer was then used as is in the pressure sensitive adhesive (PSA) formulation.

Preparation of Acrylate Functional Copolymer

The following reaction scheme shows the steps that were carried out in preparing the acrylate functional copolymer from the product mixture above:

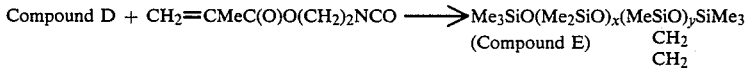
(Compound E) $CH_2$
$CH_2$
$CH_2O(CH_2CH_2O)_zC(O)NH(CH_2)_2O(O)CMe=CH_2$ The product mixture above, (97 g, ~0.1 mole of —COH) was reacted with isocyanatoethyl methacrylate (8 g, ~0.05 mole) using a procedure detailed in Lee, et al. U.S. Pat. No. 4,600,751 (July 15, 1986). The resulting reaction took place rapidly at room temperature in about 10 min. At this point, varying levels of methyl methacrylate could be added to vary the physical characteristics of the system, if desired.

Example II

Evaluation of Adhesion Properties following demonstrates the effect of varying the size and level of polyethylene oxide (PEO) grafting and the degree of polymerization (DP) of the siloxane backbone of the graft copolymer, the molecular weight (Mn) of the resinous copolymer, and the loading level of resinous copolymer on adhesion of the composition of the invention.

In these examples, G in the graft copolymer formula was —$CH_2CH_2CH_2O$—, z was 4, 8 or 12.5, and (x+y) was varied from 50 to 1000 to determine what effect graft copolymer molecular weight has on adhesion. The value of y/(x+y) varied from 0.1 to 1.

For comparison, graft copolymers having pendant side chains of the formula —$CH_2CH_2C(Me)_2OH$ were prepared in order to differentiate the effect of hydrophilicity induced by the terminal —OH group compared to that induced by both the terminal —OH group and the polyethylene oxide (PEO) group.

The molecular weight (Mn) of the resinous copolymer varied from about 2400 to 8400.

Procedure

The adhesive formulations were prepared by adding the silicate resin (in solvent) to the stripped graft copolymer, then diluting to 50% solids with Freon® fluorocarbon. None of the samples had any catalyst or crosslinker present in the formulation.

The formulations were then coated onto 8½"×11"sheets of 2 mil Type A Mylar® with a 0.003" Bird Bar Applicator. After allowing most of the solvent to evaporate off (20-30 min.), the adhesive samples were placed in an oven for 10 minutes at 100° C. Immediately after devolatilizing the samples, they were evaluated for adhesion using the following procedure:

a. cut into 1 inch strips with a tape cutter
b. adhere to a clean, stainless steel, mirror finished panel
c. draw a 4½ pound roller over the strip without application of any additional pressure
d. allow the adhesion panel to lie undisturbed for 20 minutes (normally the samples were pulled immediately due to lack of time and only two test panels)
e. peel about 1"from the panel and lay the tab back over the panel
f. attach the freed end of the panel to the lower jaw of an Instron® tensile testing apparatus (equipped with a 2000g load cell) and the freed end of the tape to the upper jaw of the Instron® apparatus
g. operate the tensile machine at 12"/min (the Instron used had to be operated at ~20"/min) and pull off the adhesive at 180° peel, then average the recorded force.

All of the adhesion values were measured in g/in.

Effect of Graft Size

A variety of graft copolymers were prepared in which the sizes of the PEO segments were varied, then they were formulated into pressure sensitive adhesives (PSA's) with resinous copolymer and evaluated for optimum adhesion. Table 1 shows that if the level of PEO grafting was held constant at 10 mole %, as the size of PEO graft was increased from 0 ethylene oxide units (10% $Z_O$) to 12 ethylene oxide units (10% $Z_{12}$), the adhesion values decreased, reaching a maximum at z=8, then decreased at z values greater than 8. However, most of the data suggests that acceptable adhesion values can be obtained even with the $Z_{12}$ formulations if a lower molecular weight resinous copolymer is used.

The 10% $Z_O$ copolymer had excellent adhesion and tack; randomly placing carbinol groups along the siloxane backbone appears to enhance the adhesion in standard PSA formulations.

Effect of Grafting Level

Since the hydrophilicity of the silicone/organic copolymers of the invention can be enhanced either by increasing the size of the PEO side chain or by increasing the number of graft sites along the siloxane backbone, the effect on adhesion of increasing the number of graft sites was also evaluated. Results are shown in Table 2. For siloxanes with a DP of 1000, as the number of graft sites was increased from 0 to 100 mole %, the adhesion values decreased with an increase in the level of grafting. For siloxanes with a lower DP, i.e. 100–500, the adhesion value remained more or less constant at about 1500 g/in up to about 60% grafting, then decreased with an increase in the level of grafting.

When 100% of one of the methyl groups in a polydimethyl siloxane (PDMS) backbone are replaced with a polyethylene oxide segment (independent of segment size) an incompatibility problem occurs and phase separation becomes an obvious problem.

Effect of DP of Siloxane Backbone

To determine the effect, if any, the molecular weight of the graft copolymer had on the resulting adhesion values, the DP of the siloxane backbone was varied between 13 and 1000 (average values). Initially it was found that the addition of the PEO segments to the siloxane backbone became more difficult as the size of the siloxane backbone was increased. Whereas the addition reaction was complete in a couple of hours at 100° C. with the lower DP polymers, the addition often took days with the 1000 DP siloxanes, and the copolymers would readily gel before the addition was complete (especially with the $Z_8$ and $Z_{12}$ PEO segments).

Although the results in Table 3 show that the range in DP evaluated had little effect on the optimum adhesion of the 10% $Z_4$ copolymers, as the size and level of the PEO segment was increased, a dramatic effect on optimum adhesion was noted. However, it was also observed that lowering the Mn of the silicate resin in the higher molecular weight $Z_8$ copolymers and the higher level of grafting copolymers would enhance the optimum adhesion value.

Effect of the Molecular Weight (Mn) of Resinous Copolymer

The effect of resinous copolymer molecular weight on adhesion was evaluated. It was found (Table 4) that as the molecular weight of the resin was decreased, the level of resin required for optimum adhesion values increased.

Effect of Hydroxyl Functionality of the Graft Segment

To determine what effect, if any, the terminal —OH functionality of the PEO segment had on the resulting adhesion, 2-methyl-2-butanol groups were attached to the siloxane backbone, at levels of 1, 5, 10, and 55 mole %, and evaluated for adhesion. The results shown in Table 5 demonstrated that excellent improvements in adhesion values could be obtained with as little as 1% carbinol functionality along the siloxane backbone; however, as the level of carbinol functionality is increased above 10 mole %, the adhesion begins to drop off.

TABLE 1

EFFECT OF GRAFT SIZE
z = 0, 4, 8 & 12.5
Resin Mn = ~5900
Siloxane DP = 100

| Graft Copolymer | SiO/PEO | Resin (Wt. %) | Adhesion (g/in) |
|---|---|---|---|
| 10% $Z_0$ | 1/0 | 55 | 1600 |
| 10% $Z_4$ | 3/1 | 60 | 1780 |
| 10% $Z_8$ | 1.8/1 | 45 | 1850 |
| 10% $Z_{12}$ | 1.2/1 | 40 | 50 |
| PDMS | — | 60 | 600 |

TABLE 2

EFFECT OF GRAFTING LEVEL
z = 4 & 8
Resin Mn ~5900
Siloxane DP = 50 to 1000

| Graft Copolymer | SiO/PEO wt % | Siloxane DP | Resin (wt %) | Adhesion (g/in) |
|---|---|---|---|---|
| 10% $Z_4$ | 3/1 | 1000 | 60 | 1750 |
| 15% $Z_4$ | 2/1 | 500 | 65 | 1500 |
| 20% $Z_4$ | 1.5/1 | 1000 | 60 | 950 |
| 27% $Z_4$ | 1.1/1 | 500 | 55 | 1500 |
| 50% $Z_4$ | 0.6/1 | 1000 | 55 | 550 |
| 55% $Z_4$ | 0.5/1 | 100 | 70 | 1500 |
| 70% $Z_4$ | 0.4/1 | 1000 | 45 | 80 |
| 70% $Z_4$ | 0.4/1 | 100 | 62 | 1200 |
| 100% $Z_4$ | 0.25/1 | 50 | resin incompatible | |
| 10% $Z_8$ | 1.8/1 | 100 | 45 | 1850 |
| 20% $Z_8$ | 0.9/1 | 100 | 65 | 1400 |
| 100% $Z_8$ | 0.15/1 | 50 | resin incompatible | |

TABLE 3

EFFECT OF SILOXANE DP
z = 4, 8, and 12.5
mole % grafting = 10 & 50
Resin Mn = 5900

| Graft Copolymer | SiO/PEO (wt %) | Siloxane DP | Resin (wt %) | Adhesion (g/in) |
|---|---|---|---|---|
| 10% $Z_4$ | 3/1 | 13 | 60 | 1800 |
| 10% $Z_4$ | 3/1 | 100 | 60 | 1780 |
| 10% $Z_4$ | 3/1 | 500 | 60 | 1700 |
| 10% $Z_4$ | 3/1 | 1000 | 60 | 1750 |
| 10% $Z_8$ | 1.8/1 | 100 | 45 | 1850 |
| 10% $Z_8$ | 1.8/1 | 1000 | 55 | 350 |
| 10% $Z_{12.5}$ | 1.2/1 | 100 | 40 | 50 |
| 50% $Z_4$ | 0.6/1 | 1000 | 55 | 550 |
| 55% $Z_4$ | 0.5/1 | 100 | 70 | 1500 |

TABLE 4

EFFECT OF MOLECULAR WEIGHT (Mn) OF RESINOUS COPOLYMER USING 10% $Z_4$ @ DP ≦ 1000

| Reference Resin | Resin Mn | Resin (wt %) | Adhesion (g/in) |
|---|---|---|---|
| 1 | 2576 | 95 | 1000 |
| 2 | 2631 | 95 | 1250 |
| 3 | 3175 | 90 | 1650 |
| 4 | 4188 | 80 | 1650 |
| 5 | 5281 | 70 | 1600 |
| 6 | 5900 | 60 | 1750 |
| 7 | 8527 | 55 | 1200 |

TABLE 5

ADHESION EVALUATION OF SILOXANE POLYMER/RESIN FORMULATIONS WITH —$CH_2CH_2CMe_2OH$ GRAFTS ALONG THE SILOXANE BACKBONE AND RESINOUS COPOLYMER

| Graft Copolymer | SiO/PEO (wt %) | Siloxane DP | Resin (wt %) | Adhesion (g/in) |
|---|---|---|---|---|
| PDMS | 1/0 | 500 | 60 | 600 |

TABLE 5-continued

ADHESION EVALUATION OF SILOXANE POLYMER/
RESIN FORMULATIONS WITH —CH$_2$CH$_2$CMe$_2$OH GRAFTS
ALONG THE SILOXANE BACKBONE AND RESINOUS
COPOLYMER

| Graft Copolymer | SiO/PEO (wt %) | Siloxane DP | Resin (wt %) | Adhesion (g/in) |
|---|---|---|---|---|
| 1% Z$_0$ | 85/1 | 500 | 65 | 1250 |
| 5% Z$_0$ | 17/1 | 500 | 50 | 1200 |
| 10% Z$_0$ | 8.3/1 | 500 | 50 | 2000 |
| 55% Z$_0$ | 1.4/1 | 100 | 0 | 85 |

Example III

Toxicity Evaluation

For use in drug delivery systems such as transdermal drug delivery devices, it is important that the adhesive compositions of the invention can be used in direct contact with a user's skin.

Adhesive compositions of the invention have been evaluated for cytotoxicity by tissue cell culture analysis and have been found to give negative responses in direct contact, thus demonstrating that the material are non-toxic.

Example IV

Evaluation of Adhesives for Water Absorption and Controlled Release of Testosterone The following tests explore the effects of (a) the size of polyethylene oxide side chains and the level of grafting, and (b) molecular weight (Mn) and loading level of resinous copolymer on both water absorption and the release rate of a slightly hydrophilic drug (testosterone) from cured membranes of the adhesive formulations.

Graft copolymers similar to those of Example II were evaluated, with the value of y/(x+y) ranging from 0.1 to 0.6.

(A) Water Absorption

Increasing the size of the PEO segments increases the hydrophilicity of the graft copolymer, thus enhancing the release of hydrophilic drugs. Also, there is a direct correlation between the amount of water absorbed by the polymer and the release rate of hydrophilic drugs from the polymer. A variety of copolymers were prepared in which (a) the size of PEO graft segments and the level of grafting, and (b) molecular weight (Mn) and the loading level of resinous copolymer were varied, then they were formulated into PSAs, cured with Lupersol 101 and methylvinylsiloxane and evaluated for water absorption.

1. Effect of Graft Segment Size

The results (Table 6) confirm that as the size of the PEO segment was increased, the amount of water absorbed by the cured adhesive formulation increased. The results also show that adding resinous copolymer to the membrane formulations significantly lowers the amount of water absorbed.

The 10% Z$_O$ copolymer, although it had excellent adhesion and tack, showed very little difference in water absorption between the filled and the unfilled samples.

As shown in Table 7, the level of water absorbed was directly proportional to the number of graft sites (from 0-70 mole %) along the siloxane backbone. As discussed above, with the addition of resinous copolymer to the membrane formulations, the water absorption is significantly reduced, especially as the level of grafting is increased above 27 mole % (16.3 wt. % CH$_2$CH$_2$O).

3. Effect of Resinous Copolymer Molecular Weight (Mn)

It was found (Table 8) that as the molecular weight of the resin was decreased, there was very little, if any, difference in the amount of water absorbed.

4. Effect of Loading Level of Resinous Copolymer

As shown in Tables 6, 7, and 8 as the loading level of resinous copolymer was increased in the membrane formulations, the water absorption decreased. This trend was further confirmed in the data shown in Table 9 which show a more direct relationship between loading level of resinous copolymer and weight % water absorbed. It was expected from these data that as the loading level of resinous copolymer (independent of resin molecular weight) was increased in an adhesive formulation, the release rate of bioactive agents would also decrease.

(B) Release Rate of Testosterone

1. Effect of PEO Segment Size

As shown in Table 10 as the size of the PEO segment was increased from 0 to 12.5 ethylene oxide repeat units, the release rate of testosterone (a hydrophilic drug) was increased by almost an order of magnitude. The release rate obtained with membranes in the absence of resinous copolymer also increased with an increase in PEO segment size. As shown in Table 10, adding resinous copolymer to the membrane formulations significantly decreased the release rate of testosterone, following the same trend as the water absorption results described above.

Also as previously, the OH functionality of the 10% Z$_O$ did not significantly affect the release rates of testosterone through these formulations although the PSA formulations did have excellent adhesion and tack.

2. Effect of Grafting Level

As shown in Table 11, the release rates of testosterone did increase as the number of graft sites increased. It also shows the dramatic reduction in release rate with the addition of resinous copolymer to the membrane formulations, especially as the level of grafting and weight % PEO were increased.

3. Effect of Resinous Copolymer Molecular Weight (Mn)

The effect of resinous copolymer on molecular weight (Mn) on the release rate is shown in Table 12. As the molecular weight of the resinous copolymer was decreased, the release rate of hydrophilic drugs was somewhat increased, especially when liquid resinous copolymer samples were evaluated. This was unexpected because the absorption of water into these filled membrane materials did not appear to be affected by the molecular weight of the resinous copolymer.

4. Effect of Loading Level of Resinous Copolymer

Data shown in Tables 6-12, indicate that as the level of resinous copolymer was increased in the membrane formulations the water absorption level and the drug release rates decreased. As shown in Table 13 the release of testosterone does not appear to be significantly reduced at the lower loading levels of resinous copolymer. However, as the loading level approached 50 weight %, the testosterone release rates drop off dramatically.

The foregoing results demonstrate that hydrophilic PSAs, formulated from the hydrophilic PDMS/PEO graft copolymers, maintained a controlled release mechanism which enhanced the release of hydrophilic drugs (testosterone) from the PSA formulations and a data base was generated for calculating desired "custom fit" formulations based on both adhesion and drug release rates.

TABLE 6
THE EFFECT OF PEO SIZE AND WEIGHT

| Graft Copolymer | Resinous Copolymer | PEO (Weight %) | % Water Absorption |
|---|---|---|---|
| 10% $Z_0$ | 50% | 0 | 1% |
| 10% $Z_0$ | — | 0 | 2 |
| 10% $Z_4$ | 50% | 9.5 | 1.5 |
| 10% $Z_4$ | — | 19.0 | 11.7 |
| 10% $Z_8$ | 50% | 15.5 | 7 |
| 10% $Z_8$ | — | 31.0 | 129 |
| 10% $Z_{12.5}$ | 50% | 29.0 | 36 |
| 10% $Z_{12.5}$ | — | 58.0 | 169 |

TABLE 7
THE EFFECT OF PEO LEVEL OF GRAFTING

| Graft Copolymer | Resinous Copolymer | PEO (Weight %) | % Water Absorption |
|---|---|---|---|
| 10% $Z_4$ | 50% | 9.5 | 1.5% |
| 10% $Z_4$ | — | 19.0 | 11.7 |
| 15% $Z_4$ | 50% | 13.0 | 4.0 |
| 20% $Z_4$ | 50% | 16.3 | 5.0 |
| 20% $Z_4$ | — | 32.5 | 15.0 |
| 27% $Z_4$ | 50% | 21.3 | 13.5 |
| 50% $Z_4$ | 50% | 28.2 | 25.0 |
| 50% $Z_4$ | — | 56.4 | 486 |
| 70% $Z_4$ | 50% | 32.8 | 60 |

TABLE 8
THE EFFECT OF RESINOUS COPOLYMER Mn

| Graft Copolymer | Resinous Copolymer Mn | Wt. % | % Water Absorption |
|---|---|---|---|
| 10% $Z_4$ | 1927 | 50% | 3% |
| 10% $Z_4$ | 2631 | 50% | 1.4% |
| 10% $Z_4$ | 3175 | 50% | 0% |
| 10% $Z_4$ | 5281 | 50% | 0% |
| 10% $Z_4$ | 5900 | 50% | 1% |
| 10% $Z_4$ | 8527 | 50% | 1% |
| 10% $Z_4$ | — | — | 11.7% |

TABLE 9
THE EFFECT OF LOADING LEVEL OF RESINOUS COPOLYMER

| Graft Copolymer | Resinous Copolymer | PEO (Weight %) | % Water Absorption |
|---|---|---|---|
| 10% $Z_4$ | 0% | 19.0 | 11.7% |
| 10% $Z_4$ | 25% | 14.3 | 3.0% |
| 10% $Z_4$ | 35% | 12.4 | 2.3% |
| 10% $Z_4$ | 50% | 9.5 | 1.5% |
| 10% $Z_{12.5}$ | 0% | 58 | 169% |
| 10% $Z_{12.5}$ | 25% | 43 | 109% |
| 10% $Z_{12.5}$ | 35% | 38 | 78% |
| 10% $Z_{12.5}$ | 50% | 29 | 36% |

TABLE 10
THE EFFECT OF PEO SIZE AND WEIGHT PERCENT

| Graft Copolymer | Resinous Copolymer | PEO (Weight %) | Testosterone Release Rate dQ/dt × 1 (× $10^5$) (mcg/cm-sec) |
|---|---|---|---|
| 10% $Z_0$ | 50% | 0 | 2.27 |
| 10% $Z_0$ | — | 0 | 1.36 |
| 10% $Z_4$ | 50% | 9.5 | 5.01 |
| 10% $Z_4$ | — | 19.0 | 33.2 |
| 10% $Z_8$ | 50% | 15.5 | 8.25 |
| 10% $Z_8$ | — | 31.0 | 38.6 |
| 10% $Z_{12.5}$ | — | 58.0 | 44.4 |

TABLE 11
THE EFFECT OF THE LEVEL OF PEO GRAFTING

| Graft Copolymer | Resinous Copolymer | PEO (Weight %) | Testosterone Release Rate dQ/dt × 1 (× $10^5$) (mcg/cm-sec) |
|---|---|---|---|
| 10% $Z_4$ | 50% | 9.5 | 5.01 |
| 10% $Z_4$ | — | 19.0 | 33.2 |
| 15% $Z_4$ | 50% | 13.0 | 5.3 |
| 15% $Z_4$ | — | 26.0 | 64 |
| 27% $Z_4$ | 50% | 21.3 | 11.5 |
| 27% $Z_4$ | — | 42.6 | 114 |
| 50% $Z_4$ | 50% | 28.2 | 22.9 |
| 50% $Z_4$ | — | 56.4 | 215 |

TABLE 12
THE EFFECT OF RESINOUS COPOLYMER Mn

| Graft Copolymer | Resinous Copolymer Mn | Wt. % | Testosternone Release Rate dQ/dt × 1 (× $10^5$) (mcg/cm-sec) |
|---|---|---|---|
| 10% $Z_4$ | 1927 | 50% | 13.6 |
| 10% $Z_4$ | 2631 | 50% | 8.53 |
| 10% $Z_4$ | 5900 | 50% | 5.01 |
| 10% $Z_4$ | 8527 | 50% | 5.08 |
| 10% $Z_4$ | — | 0% | 33.2 |

TABLE 13
THE EFFECT OF LOADING LEVEL OF RESINOUS COPOLYMER

| Graft Copolymer | Resinous Copolymer | PEO (Weight %) | Testosterone Release Rate dQ/dt × 1 (× $10^5$) (mcg/cm-sec) |
|---|---|---|---|
| 10% $Z_4$ | 0% | 19.0 | 33.2 |
| 10% $Z_4$ | 25% | 14.3 | 11.6 |
| 10% $Z_4$ | 35% | 12.4 | 10.3 |
| 10% $Z_4$ | 50% | 9.5 | 5.01 |
| 10% $Z_{12.5}$ | 0% | 58 | 44.5 |
| 10% $Z_{12.5}$ | 25% | 43 | 43.7 |
| 10% $Z_{12.5\%}$ | 35% | 38 | 31.5 |
| 10% $Z_{12.5}$ | 50% | 29 | 14.8 |

EXAMPLE V

Evaluation of Adhesives for Controlled Release of Various Drugs

This example demonstrates the usefulness of the inventive adhesive compositions in controlling the release of drugs in addition to testosterone.

The graft copolymer used was similar to that used in the examples above, and was a 10% $Z_8$ graft copolymer blended in a 50:50 weight ratio with a resinous copolymer having a molecular weight of about 5900.

The following drugs were evaluated for both capsule and matrix type release rates:

Steroids: Progesterone, testosterone, hydrocortisone, and β-Estradiol
Antihistamine: Chlorophinaramine
Antihypertensive:
Antismoking: Nicotine
Antianginal: Nitroglycerine
Antiinflammatory: Indomethacine

Capsule Type Release Mechanism

In vitro capsule type release mechanisms were determined at 37° C. using a Ghannam-Chien membrane permeation apparatus under well maintained sink conditions. The apparatus and measurement procedure are described in K. Tojo, et al., *AICHE J.*, Vol. 31, 741 (1985) and K. Tojo, et al., *J. of Cont. Rel.*, Vol. 1, 197 (1985). The release rate data were normalized for membrane thickness. In all cases, the rate pf release of the drugs from the membranes (as monitored by UV) was found to be constant and Table 14 lists the measured release rate values.

Matrix Type Release Mechanism

To demonstrate that the values obtained by capsule type release could also be achieved via matrix type mechanisms, all of the drugs were also evaluated for release from drug loaded membranes using techniques and equations derived by Langer. See Langer, *Chem. Eng. Commun.*, Vol. 6, pp.1–48 at 17–18 (1980). The results of these evaluations are shown in Table 14.

Reproducible matrix release rate values were obtained, and the measured values are in agreement with those obtained via capsule type release mechanism.

Comparison of Release Rates of Drugs from Graft Copolymer and Ungrafted Silicone Polymer Table 15, below, sets forth results comparing release rates of a hydrophobic drug (progesterone) and a hydrophilic drug (testosterone) from unfilled membranes of either a 10% $Z_8$ graft copolymer of the invention or ungrafted polydimethylsiloxane (PDMS) The results show that as the hydrophilicity of the polymer is increased (i.e. when the silicone/PEO graft copolymer is used) the release rate of hydrophobic progesterone was not significantly affected. However, the release rate of hydrophilic testosterone was significantly enhanced.

TABLE 14

RELEASE RATE OF DRUGS THROUGH A HYDROPHILIC MEMBRANE CONSISTING OF 10% $Z_8$ ELASTOMER AND 50 WT. % RESINOUS COPOLYMER

| Drug | dQ/dt × 1 (× $10^4$)(mcg/cm-sec) | |
|---|---|---|
| | Capsule | Matrix |
| Progesterone | 1.22 | 3.68 |
| Testosterone | 0.89 | 0.889 |
| Hydrocortisone | 0.63 | 0.56 |
| β-Estradiol | 4.01 | 2.97 |
| Chlorophinaramine | 17.7 | 83.0* |
| | | 204 |
| Nitroglycerine | — | 14.0 |
| Indomethacine | 21.0 | 21.4 |
| Nicotine | 66.0 | 57.9 |
| Clonidine | 67.9 | 3.5 |

*The matrix type release of chlorophinaramine was evaluated twice; however, inconsistent release rate data has been obtained due to too strong a concentration of the drug in the membranes.

TABLE 15

RELEASE RATE OF DRUGS THROUGH UNFILLED PDMS MEMBRANES AND HYDROPHILIC MEMBRANES CONSISTING OF 10% $Z_8$ ELASTOMER

| Drug | Polymer or Copolymer | dQ/dt × 1 (× $10^4$) (mcg/cm-sec) |
|---|---|---|
| Progesterone | PDMS | 5.67* |
| Progesterone | 10% $Z_8$ | 6.14 |
| Testosterone | PDMS | 0.555* |
| Testosterone | 10% $Z_8$ | 3.86 |

*Lee, et al., Drug Dev. & Ind. Pharmacy, Vol. 12, No. 3 (1986) p. 358, 360.

EXAMPLE VI

Evaluation of Adhesion Retention Upon Aging drugs identified in Example V were loaded at 10 weight percent into three adhesive formulations of the invention in which the degree of copolymer hydrophilicity was varied, with the graft copolymers designated 10% $Z_O$, 10% $Z_4$ and 40% $Z_4$. In each case, the graft copolymer was blended with a resinous copolymer having an Mn of about 5900, at a weight ratio of 40% graft copolymer/60% resinous copolymer. The resulting adhesives were monitored for adhesion versus time using the method of Example II.

The $Z_O$ copolymer was a control wherein the grafted pendant group was —$CH_2CH_2C(Me)_2OH$, and was used in order to differentiate the effect of hydrophilicity induced by the terminal —OH group alone, as compared to that induced by both terminal —OH group and the grafted ($CH_2CH_2O$)z groups.

In each graft copolymer, the average value of (x+y) was 100, with y/(x+y) varying from 0.1 and 0.4.

Initial Adhesive Evaluation

The data in column 1 of each of Tables 16–18 show that acceptable adhesion values were typically measured on most of the drug loaded adhesive matrices immediately after formulation; however, some trends were apparent. The 10% $Z_O$ formulations of Table 16 (least hydrophilic) had a higher adhesion value for an adhesive loaded with progesterone (a hydrophobic drug) than for the same formulation loaded with testosterone or hydrocortisone (hydrophilic drugs). However, as the hydrophilicity of the adhesive formulation was increased (Table 17) the trend was reversed and the adhesives loaded with the hydrophilic drugs had higher adhesion values than those loaded with hydrophobic drugs.

The data in Table 18 show that as the hydrophilicity of the adhesive formulation is increased further, adhesion of the drug loaded adhesive matrices drops off considerably for several of the drugs; however, the control (reference sample without drug) also has a lower adhesion value, which makes it reasonable to assume that the lower adhesion is at least partially a result of the adhesive formulation and that the adhesion values can be further optimized by varying the molecular weight of the silicone-PEO copolymer and/or resinous copolymer as well as the loading level of resinous copolymer in the formulation. Increasing the hydrophilicity of the adhesive increases the organic nature of the adhesive; thus, the formulations may interact differently with the drugs than a typical silicone based adhesive.

Aged Adhesive Evaluations

The data in columns 2 and 3 of Tables 16–18 show the effect of aging for one week on drug loaded adhesive formulations. When a 10% $Z_O$ formulation was used, little if any effect on adhesion was observed as the tapes were aged; however, the adhesives containing 10 wt. % indomethacine appeared to increase in adhesion to stainless steel with time, the adhesive sample loaded with chlorophinaramine dried-out in less than one week, and the adhesive sample containing β-estradiol dropped off in adhesion after one month.

Whereas little change in adhesion upon aging was observed for the drug loaded 10% $Z_O$ formulations, the samples prepared with the 10% $Z_4$ formulations (Table 17) almost all showed improvement in adhesion vs. time. Exceptions to this were adhesive samples loaded with progesterone and chlorophinaramine which both significantly lost adhesion within one week of aging, and adhesives loaded with nitroglycerine which appeared to drop in adhesion between one and four weeks of aging.

The results in Table 18 show that all of the drug loaded adhesive formulations prepared with the 40% $Z_4$ graft copolymer dried out within one week of aging.

Results presented above demonstrate that the drug loaded adhesive matrices have acceptable adhesion values. Although these results show that these adhesives possess properties desirable for a contact adhesive, and that a number of therapeutic agents can be incorporated into the PSAs without compromising the functional adhesive tape properties. Adhesive formulations should first be optimized with the drug since the optimum adhesion may also be a function of the drug loading. Then the effective range of drug loading in the formulations should be established.

The results also demonstrate that silicone-PEO resinous copolymer PSA formulations of the invention loaded with bioactive agents control the release of the bioactive agents and maintain their adhesion upon aging, thus permitting their use in transdermal polymer patch applications. This family of adhesives has a distinct advantage over typical PSA formulations because they also enhance the release rate of hydrophilic bioactive agents.

TABLE 16

ADHESION EVALUATION FOR SEVERAL DRUGS AT 10 WT. % DRUG LOADING THROUGH A 40 WT. % (10% $Z_0$)/60 WT. % RESINOUS COPOLYMER FORMULATION

| Drug | Adhesion (g/in)/Tack* | | |
|---|---|---|---|
| | No Aging | 1 Week | 4 Weeks |
| Control | 1350/1 | 1300/1 | 1400/1 |
| Progesterone | 800/2 | 500/2 | 800/2 |
| Testosterone | 40/3 | 20/4 | 20/4 |
| Hydrocortisone | 120/3 | 120/3 | 80/3 |
| β-Estradiol | 700/2 | 700/2 | 40/4 |
| Chlorophinaramine | 1800/1 | Dry | — |
| Nitroglycerine | 1300/1 | 1300/1 | 1500/1 |
| Indomethacine | 550/2 | 900/1 | 1200/1 |
| Nicotine | 1500/1 | 1900/1 | 1000/1 |
| Clonidine | >50/4 | 100/4 | 80/1 |

*Tack Rating:
1 excellent
2 good
3 fair
4 poor

TABLE 17

ADHESION EVALUATION FOR SEVERAL DRUGS AT 10 WT. % DRUG LOADING THROUGH A 40 WT. % (10% $Z_4$)/60 WT. % RESINOUS COPOLYMER FORMULATION

| Drug | Adhesion (g/in)/Tack* | | |
|---|---|---|---|
| | No Aging | 1 week | 4 weeks |
| Control | 1250/1 | 1700/1 | 1750/1 |
| Progesterone | 400/3 | 200/3 | 100/2 |
| Testosterone | 650/2 | 1000/1 | 800/2 |
| Hydrocortisone | 550/2 | 1200/1 | 1400/1 |
| β-Estradiol | 700/2 | 1200/1 | 1400/1 |
| Chlorophinaramine | 2000/1 | 500/2 | 50/4 |
| Nitroglycerine | 1950/1 | 1800/1 | 1000/1 |
| Indomethacine | 1100/1 | 1200/2 | 1700/1 |
| Nicotine | not measured | | |
| Clonidine | not measured | | |

*Tack Rating:
1 excellent
2 good
3 fair
4 poor

TABLE 18

ADHESION EVALUATION FOR SEVERAL DRUGS AT 10 WT. % DRUG LOADING THROUGH A 40% WT. % (40% $Z_4$)/60 WT. % RESINOUS COPOLYMER FORMULATION

| Drug | Adhesion (g/in)/Tack* | |
|---|---|---|
| | No Aging | 1 Week |
| Control | 850/1 | Dry |
| Progesterone | 70/3 | Dry |
| Testosterone | 40/3 | Dry |
| Hydrocortisone | 200/3 | Dry |
| β-Estradiol | 50/3 | Dry |
| Chlorophinaramine | 1400/1 | Dry |
| Nitroglycerine | 800/1 | Dry |
| Indomethacine | 45/3 | Dry |
| Nicotine | not measured | |
| Clonidine | not measured | |

*Tack Rating:
1 excellent
2 good
3 fair
4 poor

The foregoing detailed description is given for clearness of understanding only, and no unnecessary limitations should be understood therefrom, as modifications within the scope of the invention will be obvious to those skilled in the art.

We claim:

1. An adhesive composition consisting essentially of a blend of
   (A) about 10 to 99 wt. % of said composition of a random graft copolymer having the average formula

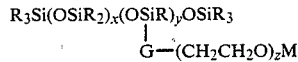

$$R_3Si(OSiR_2)_x(OSiR)_yOSiR_3$$
$$|$$
$$G-(CH_2CH_2O)_zM$$

wherein x/y is in the range of 0.01 to 100, inclusive; x+y is in the range of 10 to 1000, inclusive; z is a number less than or equal to 15; R is selected from the group consisting of alkyl radicals having 1 to 8 carbon atoms, aryl radicals and haloalkyl radicals; all R groups can be the same or different; M is H, —COCH=CH$_2$, or —CO—NH(CH$_2$)$_2$—O—CO—C(CH$_3$)=CH$_2$; G is a divalent radical selected from —CH$_2$CH$_2$CH$_2$O—, —CH$_2$CH$_2$O—, or urethane groups; and
   (B) correspondingly 1 to 90 wt. % of a random resinous copolymer consisting essentially of structural units having the formulae $R_3{}^3SiO_{0.5}$ and $SiO_2$ wherein $R^3$ is a monovalent hydrocarbon radical, said resinous copolymer having an SiOH functionality of at least about 0.5 wt. %.

2. The composition of claim 1 wherein G is a urethane group of the formula —$R^1NR^4C(0)NHR^2NHC(O)O$—wherein $R^1$ is a divalent alkylene group, $R^2$ is selected from alkylene and arylene groups and $R^4$ is H or $CH_3$.

3. The composition of claim 1 wherein said resinous copolymer of (B) comprises at least 5 wt. % of the total of (A)+(B).

4. The composition of claim 3 wherein said resinous copolymer of (B) comprises between about 30 and wt. % of the total of (A)+(B).

5. The composition of claim 1 wherein said resinous copolymer of B comprises at least about 50 wt. % of the total of (A)+(B).

6. The composition of claim 1 wherein at least a portion of said R groups comprise methyl groups.

7. The composition of claim 6 wherein substantially all of said R groups are methyl groups.

8. The composition of claim 1 wherein $R^3$ is an alkyl group having 1 to 8 carbon atoms.

9. The composition of claim 1 wherein $y/(x+y)$ is in the range of about 0.1 to 0.5, inclusive.

10. The composition of claim 1 wherein $(x+y)$ is in the range of about 10 to 500, inclusive.

11. The composition of claim 1 wherein the average value of z is in the range of about 1 to 12.5, inclusive.

12. The composition of claim 1 wherein the weight ratio of $(x+y)/z$ is about 1.5:1.

13. The composition of claim 1 wherein G is —$CH_2CH_2CH_2O$—.

14. The composition of claim 1 wherein said resinous copolymer of (B) has a number average molecular weight (Mn) in the range of about 2000 to 9000.

15. The composition of claim 14 wherein said Mn is in the range of about 2000 to 6000.

16. The composition of claim 14 wherein the molar ratio of $R_3^3SiO_{0.5}$ units to $SiO_2$ units in said resinous copolymer of (B) is in the range of about 0.6 to about 2.0.

17. The composition of claim 14 wherein the SiOH functionality of said resinous copolymer of (B) is in the range of about 0.5 to 5 wt. %.

18. The composition of claim 17 wherein said SiOH functionality is in the range of about 1 to 3 wt. %.

19. The composition of claim 1 wherein said resinous copolymer of (B) is endcapped.

20. The composition of claim 19 wherein said endcapping is present in the form of a functionality selected from hydroxyl, vinyl, acrylate, and mercapto groups.

21. The composition of claim 1 wherein at least one of said graft and resinous copolymers is crosslinked.

22. The composition of claim 21 in the form of a membrane.

23. The composition of claim 1 wherein M is —$COCH=CH_2$.

24. The composition of claim 23 wherein M is —$CO-NH(CH_2)_2-O-CO-C(CH_3)=CH_2$.

* * * * *